(12) United States Patent
Arendash et al.

(10) Patent No.: US 11,813,472 B2
(45) Date of Patent: Nov. 14, 2023

(54) SYSTEMS FOR SENSING PROPER EMITTER ARRAY PLACEMENT

(71) Applicant: NeuroEM Therapeutics, Inc., Phoenix, AZ (US)

(72) Inventors: Gary W. Arendash, Phoenix, AZ (US); Rob Baranowski, Valley Center, CA (US)

(73) Assignee: NeuroEM Therapeutics, Inc., Tampa, FL (US)

( * ) Notice: Subject to any disclaimer, the term of this patent is extended or adjusted under 35 U.S.C. 154(b) by 1075 days.

(21) Appl. No.: 16/359,749

(22) Filed: Mar. 20, 2019

(65) Prior Publication Data

US 2019/0217111 A1    Jul. 18, 2019

Related U.S. Application Data

(63) Continuation-in-part of application No. 14/205,333, filed on Mar. 11, 2014, now Pat. No. 10,765,879.

(Continued)

(51) Int. Cl.
*A61N 2/00* (2006.01)
*A61B 5/00* (2006.01)
(Continued)

(52) U.S. Cl.
CPC ............ *A61N 2/004* (2013.01); *A61B 5/6803* (2013.01); *A61N 1/0476* (2013.01); *A61N 1/08* (2013.01);
(Continued)

(58) Field of Classification Search
CPC ...... A61N 1/08; A61N 1/0476; A61N 1/3603; A61N 1/40; A61N 2/004;
(Continued)

(56) References Cited

U.S. PATENT DOCUMENTS 6,248,126 B1   6/2001 Esser
6,334,069 B1 * 12/2001 George ................... A61N 1/40
                                                              607/2

(Continued)

FOREIGN PATENT DOCUMENTS

EP    1907052       1/2010
EP    1606010 B1    2/2012

(Continued)

OTHER PUBLICATIONS

Nguyen, et al; "The Effect of a High Frequency Electromagnetic Field in the Microwave Range on Red Blood Cells"; Sep. 7, 2017.

(Continued)

*Primary Examiner* — Carl H Layno
*Assistant Examiner* — Jane C Kalinock
(74) *Attorney, Agent, or Firm* — Nathan G. Guymon, Esq.; Bamert Regan PLLC

(57) ABSTRACT

In one example in accordance with the present disclosure, an emitter system is described. The emitter system includes an array of emitters. Each emitter emits waves towards a target surface. The emitter system also includes a control system. The control system includes a sensing system to determine whether emitters in the array are properly positioned relative to the target surface. A controller of the control system adjusts emitter sets of the array of emitters based on an output of the sensing system.

19 Claims, 13 Drawing Sheets

Related U.S. Application Data

(60) Provisional application No. 61/776,097, filed on Mar. 11, 2013.

(51) Int. Cl.
*A61N 1/08* (2006.01)
*A61N 1/40* (2006.01)
*A61N 1/04* (2006.01)
*A61N 1/36* (2006.01)
*A61N 5/06* (2006.01)

(52) U.S. Cl.
CPC ............. *A61N 1/3603* (2017.08); *A61N 1/40* (2013.01); *A61N 2005/0626* (2013.01); *A61N 2005/0647* (2013.01)

(58) Field of Classification Search
CPC .... A61N 2005/0626; A61N 2005/0647; A61B 5/4082; A61B 5/4088; A61B 5/4836; A61B 5/4848; A61B 5/6803; A61B 5/6844
USPC ........................................................ 607/154
See application file for complete search history.

(56) References Cited

U.S. PATENT DOCUMENTS

| | | |
|---|---|---|
| 6,410,137 B1 | 6/2002 | Bunyan |
| 6,463,336 B1 | 10/2002 | Mawhinney |
| 6,876,337 B2 | 4/2005 | Larry |
| 7,672,648 B1 | 3/2010 | Groe |
| 8,684,901 B1 | 4/2014 | Zabara |
| 8,868,177 B2 | 10/2014 | Simon et al. |
| 9,672,393 B1 | 6/2017 | Zhu |
| 10,792,483 B2 | 10/2020 | Andocs |
| 10,850,096 B2 | 12/2020 | Teng |
| 11,058,886 B1 | 7/2021 | Matloubian |
| 11,229,788 B1 | 1/2022 | John |
| 2004/0122281 A1 | 6/2004 | Fischell |
| 2004/0127895 A1 | 7/2004 | Flock |
| 2004/0176805 A1 | 9/2004 | Whelan |
| 2004/0181115 A1 | 9/2004 | Sandyk et al. |
| 2004/0199070 A1 | 10/2004 | Krockel |
| 2005/0228209 A1 | 10/2005 | Schneider |
| 2007/0244530 A1 | 10/2007 | Ren |
| 2008/0269851 A1 | 10/2008 | Deem |
| 2009/0131739 A1 | 5/2009 | Shalev |
| 2009/0156884 A1 | 6/2009 | Schneider |
| 2009/0276019 A1 | 11/2009 | Perez |
| 2010/0042168 A1* | 2/2010 | Pasche ...................... A61N 5/00 607/2 |
| 2010/0114086 A1 | 5/2010 | Deem et al. |
| 2010/0210894 A1 | 8/2010 | Pascual-Leone |
| 2011/0230701 A1 | 9/2011 | Simon et al. |
| 2012/0065456 A1 | 3/2012 | Arendash et al. |
| 2012/0089201 A1 | 4/2012 | Pilla |
| 2012/0172954 A1 | 7/2012 | Zastrow |
| 2012/0289869 A1 | 11/2012 | Tyler |
| 2013/0237742 A1 | 9/2013 | Capstick |
| 2014/0187851 A1 | 7/2014 | Cetroni |
| 2014/0228620 A1 | 8/2014 | Vasishta et al. |
| 2014/0303425 A1* | 10/2014 | Pilla ...................... A61B 6/037 600/15 |
| 2014/0330353 A1 | 11/2014 | Knight |
| 2015/0209566 A1 | 7/2015 | Peyman |
| 2015/0342661 A1 | 12/2015 | Ron Edoute |
| 2016/0022976 A1 | 1/2016 | Peyman |
| 2016/0106997 A1 | 4/2016 | Arendash et al. |
| 2017/0014637 A1 | 1/2017 | Basser |
| 2017/0065326 A1 | 3/2017 | Rosen |
| 2017/0209579 A1 | 7/2017 | Curley |
| 2019/0030354 A1 | 1/2019 | Turner |
| 2019/0290355 A1 | 9/2019 | Amos |
| 2020/0038509 A1 | 2/2020 | Corr |
| 2020/0078600 A1 | 3/2020 | Dinh |
| 2020/0155061 A1* | 5/2020 | Pradeep ............... A61B 5/6803 |
| 2020/0164195 A1 | 5/2020 | Lowsky |
| 2020/0297286 A1 | 9/2020 | Costa |
| 2020/0346028 A1 | 11/2020 | Arendash et al. |
| 2020/0360709 A1* | 11/2020 | Luttrull .................. A61N 1/403 |
| 2021/0153925 A1 | 5/2021 | Kim |
| 2021/0177491 A1 | 6/2021 | Onik |
| 2021/0220480 A1 | 7/2021 | Peyman |
| 2021/0338265 A1 | 11/2021 | Cohn |

FOREIGN PATENT DOCUMENTS

| | | |
|---|---|---|
| EP | 2414038 | 2/2012 |
| WO | WO-2007044386 | 4/2007 |
| WO | 2008008545 A3 | 9/2008 |
| WO | WO-2008141296 | 11/2008 |
| WO | 2017157874 A1 | 9/2017 |
| WO | 2020102312 A1 | 5/2020 |
| WO | 2020141527 A1 | 7/2020 |
| WO | 2020180653 A1 | 9/2020 |

OTHER PUBLICATIONS

Karsten, et al; "Red Blood Cells are Dynamic Reservoirs of Cytokines"; Feb. 15, 2018.

Gary W. Arendash, "Transcranial Electromagnetic Treatment Against Alzheimber's Disease: Why it has the Potential to Trump Alzheimer's Disease Drug Development," Journal of Alzheimer's Disease, 32 (Jun. 2012) pp. 243-266.

Rasouli; "Attenuation of interleukin-1beta by pulsed electromagnetic fields after traumatic brain injury"; Neuroscience Letters 519 (2012) 4-8.

Merighi; "Signaling pathways involved in anti-inflammatory effects of Pulsed Electromagnetic Field in microglial cells"; Cytokine 125 (2020) 154777.

Peng Lihong et al., The Effect of Pulsed Electromagnetic Fields on Angiogenesis. Bioelectromagnetics, 42: 250-258, 2021, p. 251, col. 1, paragraph 3, col. 2, paragraphs 2-3, p. 254, col. 2, paragraph 2, p. 257, col. 2, paragraph 2.

Das Neves Sofia Pereira et al., CNS-Draining Meningeal Lymphatic Vasculature: Roles, Conundrums and Future Challenges, Frontiers Pharmacology, Apr. 28, 2021, vol. 12, p. 3, col. 1, last paragraph, p. 8, col. 2, last paragraph, p. 9, col. 1, paragraph 1.

Gerstner Elizabeth R. et al., AntiEndothelial Growth Factor Therapy for Malignant Glioma, Curr Neurol Neurosci Rep. May 2009, 9(3):254-262, p. 2, paragraphs 2-3.

* cited by examiner

SYSTEMS FOR SENSING PROPER EMITTER ARRAY PLACEMENT

RELATED APPLICATIONS

The present application claims benefit and is a continuation in part of U.S. application Ser. No. 14/205,333 filed Mar. 11, 2014 now, U.S. Pat. No. 10,765,879, which claims the benefit of U.S. Provisional Application No. 61/776,097, filed Mar. 11, 2013. These applications are incorporated herein by reference in their entireties.

BACKGROUND

Someone in the world develops Alzheimer Disease (AD) every 3 seconds. AD, the most common form of dementia, is a debilitating neurodegenerative disease in which one experiences confusion, memory impairment, language difficulty, and loss of bodily functions—often becoming fully dependent on others within 4 to 5 years of diagnoses. AD is responsible for 1 in 3 deaths of seniors and kills more people than breast and prostate cancer combined. Today, it is estimated that over 50 million people worldwide are living with AD—the prevalence is rising at an alarming rate and expected to double in the next 30 years.

Pharmaceutical companies have traditionally led the AD research effort. However, after tens of billions of dollars in research, AD remains neither preventable, curable, or even able to be slowed. An effective treatment or cure for AD is estimated to be worth more than $20 b per year. Sadly, there are no products on the market that have been proven to cure the disease or even slow disease progression.

Other neuro-degenerative disease and neurological conditions similarly plague society with current treatments and/or cures proving ineffective.

BRIEF DESCRIPTION OF THE DRAWINGS

The accompanying drawings illustrate various examples of the principles described herein and are part of the specification. The illustrated examples are given merely for illustration, and do not limit the scope of the claims.

Figure 1:
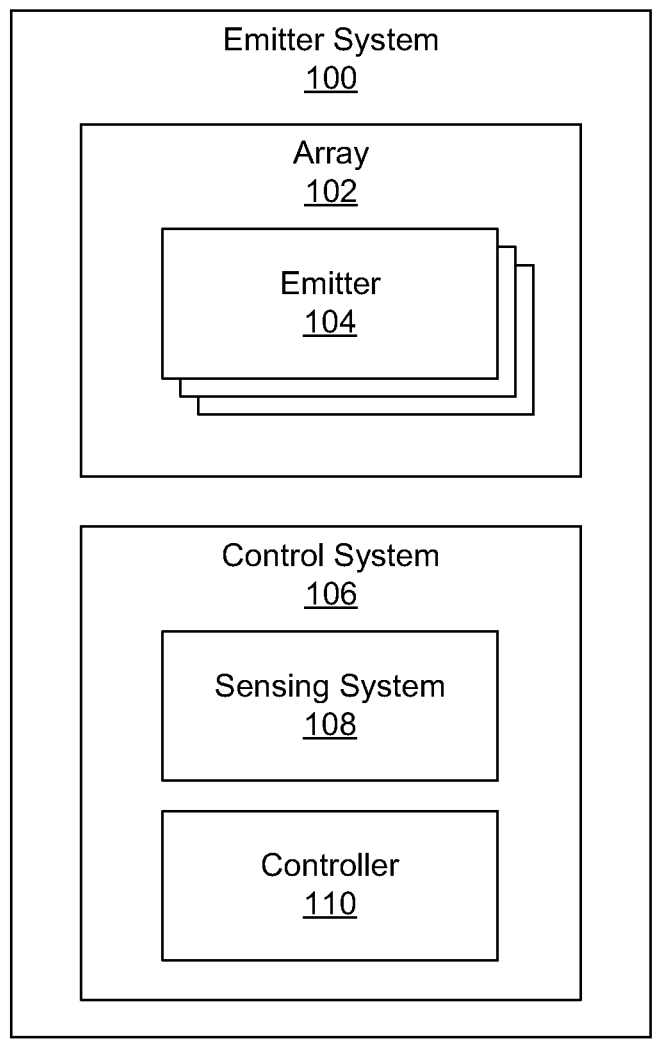
FIG. 1 is a block diagram of an emitter system, according to an example of the principles described herein.

Throughout the drawings, identical reference numbers designate similar, but not necessarily identical, elements. The figures are not necessarily to scale, and the size of some parts may be exaggerated to more clearly illustrate the example shown. Moreover, the drawings provide examples and/or implementations consistent with the description; however, the description is not limited to the examples and/or implementations provided in the drawings.

DETAILED DESCRIPTION

Alzheimer's Disease (AD) is a neuro-degenerative disease which affects millions of lives and for which no pharmaceutical cure or treatment has been found. Where pharmaceutical solutions have failed, the innovative medical device as described herein, which uses Transcranial Electromagnetic Treatment (TEMT), provides a solution. The device shows unique potential to slow and/or potentially even reverse the effects of AD. The present device includes a skull cap affixed with multiple transmitting emitters connected to a control box which may be worn on the arm. In some examples, the transmitting emitters are radio wave transmitting antennae, however in other examples the electromagnetic waves may be applied at other frequencies or may be other types of waves entirely. In these other examples, the system may include other components, such as coils or contact patches instead of antennas. The control system may include different components as well and may be placed at different locations on a patient's body. Treatment may be administered in-home by the patient's caregiver rather than through an out-patient facility. The device of the present specification, is the only technology under clinical development that targets both presumed causes of AD—the build-up of small β-amyloid (Aβ) oligomers and tau oligomers within nerve cells. A wide spectrum of pre-clinical studies show that the TEMT device has beneficial cognitive impact linked to disaggregation of toxic protein oligomers (especially Aβ) and brain mitochondrial enhancement in Alzheimer's animal models.

While specific reference is made to AD, the present system is also for the treatment of other neuro-degenerative diseases or neurological conditions such as Mild Cognitive Impairment (MCI), Mixed AD/Vascular Dementia, Cerebral Amyloid Angiopathy, Hemorrhagic Stroke, Multi-Infarct Dementia, Parkinson's Disease, Lewy Body Dementia, Down's Syndrome, Traumatic Brain Injury, Fronto-Temporal Lobe Dementia, Cerebral Traumatic Encephalopathy, Huntington's Disease, or Prion Diseases (Transmissive Spongiform Encephalopathy, Kuru, and Creutzfedt-Jakob Disease), Amyotrophic Lateral Sclerosis (ALS), mental retardation, stroke, autism, bipolar disorder, schizophrenia, anxiety disorders, mitochondrial encephalomyopathies, epilepsy, migraine headache, major depression, Dystonia, and Hemiballismus, Age-Associated Memory Impairment (AAMI), normal/unimpaired cognitive function, or subnormal cognitive function.

The mechanism whereby a TEMT device disaggregates both small (soluble) and large (insoluble) aggregates of Aβ and tau appears to involve destabilization of hydrogen bonds that keep the individual toxic protein monomers aggregated in a beta-pleated sheet formation. Electromagnetic waves around the general frequency utilized by a TEMT head device (around 1 Gz) likely do not have the ability to directly and immediately break such hydrogen bonds. Rather, these electromagnetic waves continually weaken the hydrogen bonds through vibration/resonance and dipole/dipole interactions over the course of days, weeks, and months, resulting in eventual hydrogen bond breakage and resultant disaggregation of these toxic proteins.

In order to deliver full brain TEMT, the device provides sequential, activation of multiple emitters positioned within the head cap. In some examples just one emitter is active at any given time and in other examples, multiple emitters may be active at any given time.

To obtain maximum treatment benefit of the TEMT device, the amount of power that radiates from the emitters on the head cap to the head of the patient should be maximized. For example, any energy that is directed away from the head results in a lower dosage of energy for the patient, thus reducing the overall effectiveness of the treatment.

In general, the TEMT device uses a transmitter, such as an RF transmitter, and radiating emitters, such as RF antennas, to generate and radiate the treatment into the brain of the patient. While RF transmitters may be able to measure the power that is being driven into the emitters, RF transmitters generally have very little visibility as to where the power flows once the waves pass to the air. The functionality of a properly applied head cap is that the emitters radiate power towards the head of the patient, coupling to the air between the antenna and patient's hair. That is, once the RF waves start traveling in the air, they fall incident onto the patient's hair, scalp, and skull, and penetrate into the brain where the reversing effect occurs.

However, if the head cap is not properly applied to a patient, there may be a large gap between the emitters and the patient's head. Accordingly, the amount of power that falls incident on the patient's head is decreased by the propagation loss of the waves traveling a greater distance in the air before reaching the skull.

Even worse, if the patient is not wearing the head cap and the treatment system is activated, the energy of the treatment will go to waste as it is not being applied to the patient's head as intended. That is, the TEMT device will generate the correct amount of power, will drive that power into the emitters, the emitters will radiate that power to the air, but the device will not be able to detect that the power is not getting to the patient's head to provide treatment. In this example, the life of the device may be reduced as emitters are active during non-treatment periods, i.e., when the patient is not actually wearing the head cap.

Accordingly, the present systems and methods detect if the head cap, or other treatment unit, is properly applied to the patient as treatment is being administered. If the device detects that the treatment unit is not worn properly, 1) treatment may be suspended and the patient and caregiver may be notified such that the treatment unit may be applied properly before continuing treatment or 2) treatment may be adjusted accordingly.

The present specification describes systems, methods, and devices that address the above-described problems and others. Specifically, the present specification describes a method and system for determining when an emitter system is properly applied to a subject.

Specifically, the present specification describes an emitter system. The emitter system includes an array of emitters. Each emitter is to emit waves towards a target surface. The emitter system also includes a control system. The control system includes a sensing system to determine whether emitters in the array are properly positioned relative to the target surface and a controller to adjust emitter sets of the array of emitters based on an output of the sensing system.

The present specification also describes a method. According to the method, information related to a position of emitters within the emitter array relative to a target surface is received from a sensing system of an emitter array. From the received information, it is determined whether the array is properly positioned relative to the target surface. Remedial action is taken when the received information indicates at least one emitter in the emitter array is improperly positioned relative to the target surface.

The present specification also describes an electromagnetic treatment system. The system includes a treatment unit to be worn by a subject. The treatment unit includes a material to be placed proximate to a treatment surface and an array of antennas, each antenna to emit electromagnetic waves towards the treatment surface. The treatment system also includes a control system. The control system includes a single transmitter to drive the antennas, a switching device to direct a control signal to a selected antenna set, a sensing system to determine whether antennas in the array are properly positioned relative to the treatment surface, and a controller to adjust antenna sets of the array of antennas based on an output of the sensing system.

In another example, an electromagnetic treatment system includes a treatment unit to be worn by a subject. The treatment unit includes a material to be placed proximate a treatment surface and an array of at least one antenna. In this example, each antenna emits electromagnetic waves towards the treatment surface, wherein the treatment disaggregates toxic protein aggregates, which toxic protein aggregates may be a cause of neurodegenerative diseases and impaired cognitive function. Such disaggregation may be done by destabilizing the hydrogen bonds Turning now to the figures, FIG. 1 is a block diagram of an emitter system (100), according to an example of the principles described herein. The emitter system (100) includes an array (102) of emitters (104). Each emitter (104) is to emit waves. The emitters (104) may be of varying types. For example, the emitters (104) may be antennae that emit radio frequency waves, or other frequency waves. In another example, the emitters (104) may be coils that emit magnetic waves. That is, the emitters (104) may emit different types of waves including electromagnetic and magnetic. Note that while the present specification may describe a particular type of wave, such as electromagnetic, the system and method as described herein, may implement other types of waves such as magnetic waves.

As described above, the TEMT device as described herein operates in a unique fashion such that emitters (104) are positioned in various positions relative to a target surface. For example, the emitter system (100) may include a head cap that is worn by a subject. In this example, the emitters (104) emit the waves towards the head. In another example, the emitter system (100) may be a unit to be worn around another portion of the subject's body. For example, the emitter system (100) may be disposed in a material to be wrapped around a knee of a subject. In this example, the target surface would be the skin around the knee of the subject. As can be imagined, the emitters (104) of the emitter system (100) may be positioned around a variety of target treatment surfaces.

The emitter system (100) also includes a control system (106) which includes a controller (110) to adjust emitter sets of the array (102) of emitters (104). This selective adjustment may be based on an output of a sensing system (108).

Specifically, the controller (110) passes a control signal to a transmitter which drives the emitter sets. More detail regarding the transmitter and control signal is described below in connection with FIG. 2.

As described above, the control system (106) includes a sensing system (108) to determine whether the emitters (104) in the array (102) are properly positioned relative to the target surface. That is, as described above, if the emitters (104) are not properly positioned, treatment may be less effective. In some cased, if placement of the emitters (104) is sufficiently improper, no treatment may occur as the effect of the emitters (104) is completely nullified by the improper placement. Accordingly, the sensing system (108) detects the proper or improper placement of the emitters (104) such that treatment as intended may be administered to a particular subject. In some examples, as depicted in FIG. 1, an input to the sensing system (108) may be directly from the array (102). In other examples, it may be embodied in a switching device.

Accordingly, the present specification describes a system and method for detection of proper application of the TEMT head cap or other treatment unit. Detection schemes may fall into one of several categories, several of which are described here as examples. However, additional or different sensing system (108) mechanisms may be similarly implemented in accordance with the principles described herein.

The sensing mechanism of the sensing system (108) may be of a variety of types. For example, the sensing system (108) may involve the measurement of received or reflected power from the emitters (104). This is advantageous as it does not require circuitry that is substantially different than what is used for treatment signals. Moreover, such a sensing system (108) may rely on a waveform already used for treatment, and therefore not rely on a new waveform generation. Additional details regarding such a reflected sensing system (108) is provided below in connection with FIG. 5.

As described above, the actions of the controller (110) may be based on an output of the sensing system (108). That is, the controller (110) may stop or alter the activation of the emitters (104) based on the output. Additional details on the adjustment to the operation of the emitters (104) is provided below in connection with FIG. 3.

In one specific example, a TEMT device has an emitter system (100) with 8 emitters (104), and cycles through each emitter (104) at a rate of 217 Hz. This means that each emitter (104) is activated every 4.6 milliseconds (mS). Thus, in this example, each emitter (104) may be on for a duration of 576 microseconds (μS), which is equivalent to 4.6 milliseconds (mS) divided by 8 emitters (104). It may be desirable to have at least one emitter (104) active for 99% of the time to maximize the efficacy of the treatment session, which translates to needing to switch between emitters (104) in about 5 μS for an 8 emitter case.

Figure 2:
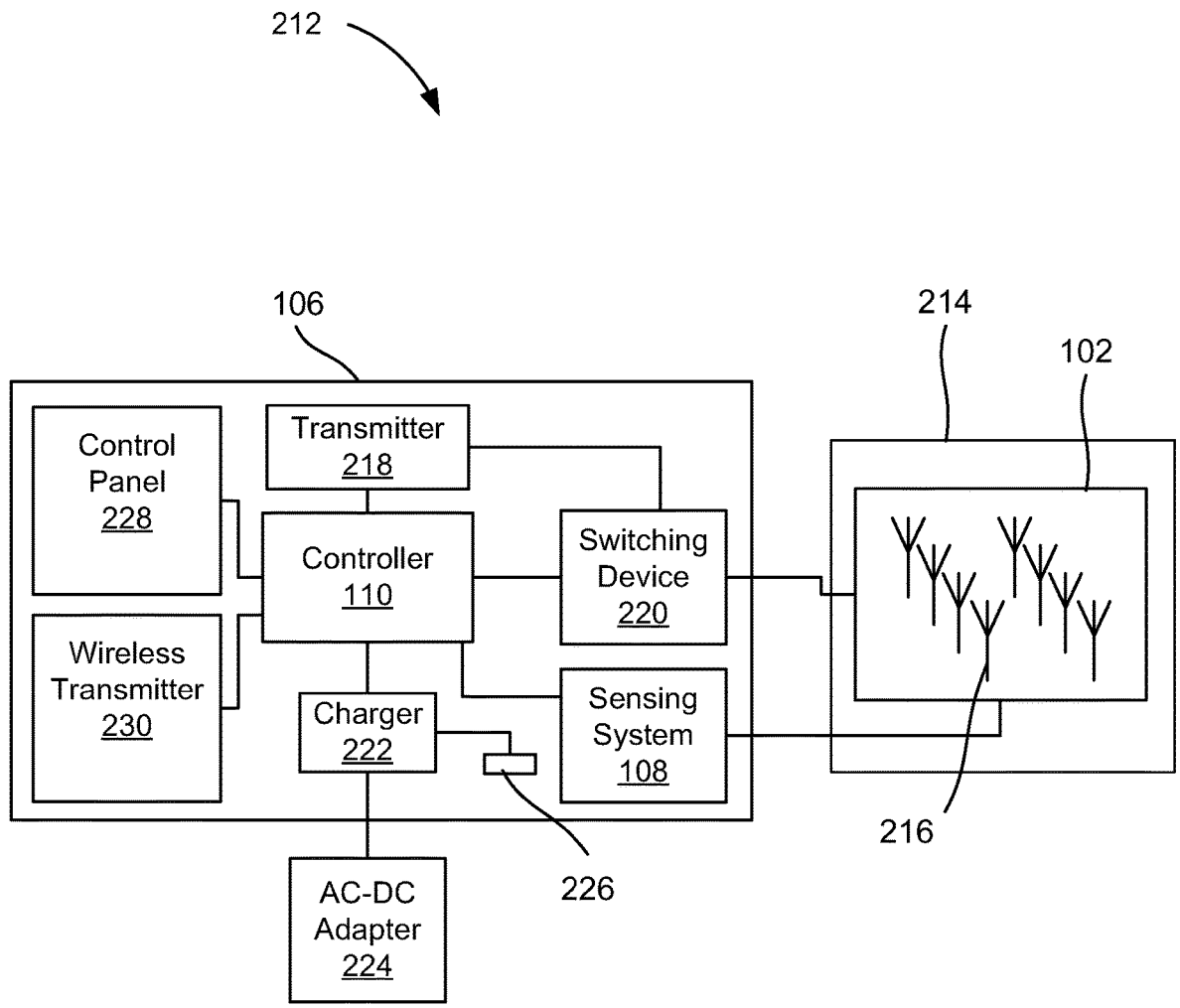
FIG. 2 is a diagram of an electromagnetic treatment system, according to another example of the principles described herein.

FIG. 2 is a diagram of an electromagnetic treatment system (212), according to another example of the principles described herein. The electromagnetic treatment system (212), or TEMT device, for the treatment of Alzheimer's and other diseases and conditions that incorporates the present system is a device that includes an electronic control system (106) and a treatment unit (214) to be worn by a subject. While specific reference is made to a head cap as a treatment unit (214) to be worn by the subject, the treatment unit (214) may be worn about other parts of the body as well. In this example, the treatment unit (214) includes emitters (FIG. 1, 104) in the form of antennas (216) for radiating electromagnetic waves, such as radio-frequency waves, into the brain. These antennas (216) can be activated sequentially and/or in combination to produce a radiation pattern that is used as a treatment to the brain. The amount of power that radiates from each antenna (216) may be controlled so that the treatment applied matches what is prescribed and is not too little or too much compared to what is desired. As described above, while FIG. 2 depicts antennas (216) other types of emitters (FIG. 1, 104) may be used as well.

FIG. 2 depicts three components of the electromagnetic treatment system (212), which are the control system (106), the treatment unit (214) with the array of antennas (216) each to emit electromagnetic waves towards the treatment surface, and the AC-DC adapter (224) that plugged into the wall and charges the control system (106). During a treatment, the treatment unit (214) in which the array (102) is disposed is worn by the patient and the control system (106) may be attached to the patient's arm, for example with a hook and fastener strip. Between treatments, the control system (106) is connected to the AC-DC adapter (224) for charging.

As described above, the control system (106) includes the controller (110) which manages the treatments, schedules, and user interface. That is, the controller (110) selectively activates antenna (216) sets of the array (102) of antennas (216) based on an output of the sensing system (108).

FIG. 2 depicts the transmitter (218) of the control system (106). In some examples, the electromagnetic treatment system (212) includes a single transmitter (218) that drives multiple antennas (216). A small and low cost TEMT unit drives the need for the control system (106) to use a single transmitter (218) and to have that transmitter's (218) output distributed to each antenna (216) at the appropriate time or with the appropriate power level and phase combination. This architecture is preferred over one that employs a dedicated transmitter for each antenna when the design goals of lower size and cost are taken into account.

For driving multiple antennas (216) at the same time for directing treatment to a certain location, the control system (106) includes a switching device (110) which may select which of the multiple antennas (216) is to be activated at a given time. That is, over the course of a treatment session, sequences of groupings of antennas (216) may be activated. The transmitter (218) generates the signal, and the switching device (220) allows the signal to be passed to particular antennae (216).

During a treatment, the controller (110) enables the transmitter (218) to generate and amplify the desired waveforms as per the treatment parameters. A power amplifier (PA) of the transmitter (218) then amplifies the signal to the levels desired for treatment. The PA output is fed into the switching device (220), which directs the signal to the appropriate antenna (216) within the antenna array (102) located in the treatment unit (214). The switching device (220) can have a purely switching function, but could also control power, and could also control phase to the different antennas (216) in the antenna array (102). That is, the controller (110) may vary a phase of an RF treatment to each antenna (216) within an antenna set, and may vary a power of the RF treatment for each antenna (216) within an antenna set to control a relative power between each antenna set. The control system (106) may also include a control panel (228) that provides the interface to the user, is used to start or stop treatments, and provides feedback and information to the user, such as treatment status and battery level.

The control system (106) may be powered by an internal battery (226) that provides enough power to run the control system (106) and complete the treatments. The charging device (222) charges the battery (226) when the AC-DC adapter (224) is present. In one example, the controller (110) gets charge status and AC-DC adapter (224) presence from the charging device (222) and displays status on the control panel (228).

In some examples, information regarding the status of the array (102) may be passed to a remote site via, for example, a wireless transmitter (230). Such a wireless transmitter (230) maintains connectivity to a local wireless network. Once this connection is established, the control system (106) may share treatment details, share device status, and even download new treatment parameters. Treatment details may include treatment schedules, durations, head cap application quality, and any adjustments made to treatment parameters due to head cap application quality.

Figure 3:
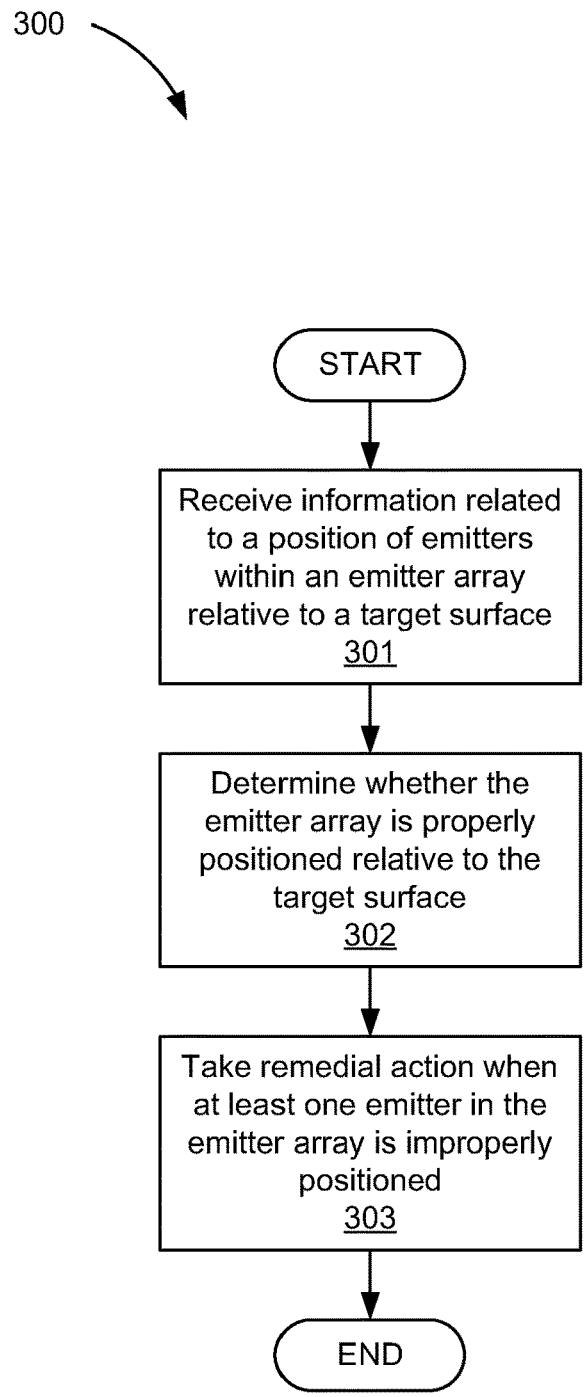
FIG. 3 is a flowchart of a method of controlling the emitter system, according to an example of the principles described herein.

FIG. 3 is a flowchart of a method (300) of controlling the emitter system (FIG. 1, 100), according to an example of the principles described herein. According to the method (300), information is received (block 301) regarding a position of the emitters (FIG. 1, 104) within the emitter array (FIG. 1, 102). Specifically, their position relative to a target surface. Such information is received from the sensing system (FIG. 1, 108) which as described above may be of a variety of types. For example, the sensing system (FIG. 1, 108) may detect reflected power from the actively emitting emitter (FIG. 1, 104). In another example, the sensing system (FIG. 1, 108) may detect power received at inactive emitters (FIG. 1, 104) to measure the active emitter (FIG. 1, 104) radiation. That is, the power received on the other side of the head will be higher if the head cap is not applied properly and the power is not being absorbed by the brain. Using this method, the highest quality application will result in the lowest power received on the other side of the head from the active antenna (FIG. 2, 216).

In another example, a capacitive loading on each emitter (FIG. 1, 104) may be determined. In yet additional examples, the sensing system (FIG. 1, 108) may include transmitter/receiver pairs of different waveforms, photodetectors, and/or mechanical sensing systems. For example, proximity sensors can be used to determine quality of application by determining the distance from the head cap to the scalp. Accordingly, how the information is received (block 301) is dependent upon the sensing system (FIG. 1, 108) that is used. In general, the information received (block 301) indicates a placement of the emitter (FIG. 1, 104) relative to the target, or treatment surface.

It can then be determined (block 302) whether the emitter array (FIG. 1, 102) is properly positioned relative to the target surface. That is, the controller (FIG. 1, 110) may include a database of expected, or satisfactory, sensing system (FIG. 1, 108) outputs. For example, the controller (FIG. 1, 110) receives from the sensing system (FIG. 1, 108) actual outputs and compares them against the target, reference, expected, or satisfactory outputs to determine (block 302) whether the emitter array (FIG. 1, 102) is properly positioned. Any variation between the actual and reference values indicates a degree of improper placement and/or a quality of the emitter array (FIG. 1, 102) application. If the variation is greater than a threshold amount, the controller (FIG. 1, 110) may take (block 303) any sort of remedial action.

Returning to the reception (block 301) of information and determination (block 302) of proper placement based on that information. As described above, in some examples the sensing system (FIG. 1, 108) may rely on a reflected power at an active emitter (FIG. 1, 104) or a power received at an inactive emitter (FIG. 1, 104). In this example, receiving information (block 301) related to a position of the emitters (FIG. 1, 104) within the emitter array (FIG. 1, 102) relative to the target surface includes receiving measurements indicating power reflected from an active emitter (FIG. 1, 104) onto an active emitter (FIG. 1, 104) or received from the active emitter (FIG. 1, 104) at an inactive emitter (FIG. 1, 104). Determining (block 302) whether the emitter array (FIG. 1, 102) is properly positioned includes therefore comparing these measurements against a reference value. Again, if they are different past a threshold amount, any variety of remedial action may be taken (block 303). Additional examples of reflected or received power being used to determine proper emitter (FIG. 1, 104) placement is provided below in connection with FIG. 5.

In another example, the sensing system (FIG. 1, 108) may rely on a capacitive loading of each emitter (FIG. 1, 104) to determine proper positioning. In this example, a signal is passed to a capacitive surface near the emitter (FIG. 1, 104). The signal may be at a frequency that is less than a control signal from the transmitter (FIG. 2, 218) to drive the emitter array (FIG. 1, 102). In another example, the signal passed may be the control signal from the transmitter (FIG. 2, 218).

In this example, receiving information (block 301) related to a position of the emitters (FIG. 1, 104) within the emitter array (FIG. 1, 102) relative to the target surface includes receiving a capacitive loading measurement for each emitter (FIG. 1, 104) from the sensing system (FIG. 1, 108). Determining (block 302) whether the emitter array (FIG. 1, 102) is properly positioned includes therefore comparing these capacitive loading measurements against a reference value. Again, if they are different past a threshold amount, any variety of remedial action may be taken (block 303). Additional examples of capacitive loading being used to determine proper emitter (FIG. 1, 104) placement is provided below in connection with FIG. 6.

Several of the detection methods detailed here, specifically those in the proximity sensor category, are beneficial in that they may produce an analog output that can be interpreted as a distance measurement between an emitter (FIG. 1, 104) and the target surface, such as a scalp. For example, capacitive sensing shows a higher capacitance as the sensor approaches the target surface. Ultrasonic sensors receive an echo sooner as the detected object gets closer. This distance from any of these sensors can be used to assign a rating about how well the treatment unit (FIG. 2, 214) is applied. For example, if one side of the head shows short distances to the scalp but the other side does not, it may not be perceived as a very good application. The data can be used to generate a 'quality' of application, where the better the head cap is applied, the higher the quality of application.

When the received information indicates at least one emitter (FIG. 1, 104) in the emitter array (FIG. 1, 102) is improperly positioned relative to the target surface, a variety of remedial actions may be taken (block 303), such as preventing activation of an improperly positioned emitter (FIG. 1, 104), or the entire array (FIG. 1, 102), and providing a notification of the improperly positioned emitter (FIG. 1, 104). That is, the proper placement determination (block 302) is used as a pass or fail indicator. If the treatment unit (FIG. 2, 214) is applied properly, the treatment continues, but if the treatment unit (FIG. 2, 213) is not applied properly, treatment is suspended and the user is notified.

In another example, the remedial action is to adjust operation parameters for an improperly positioned emitter (FIG. 1, 104). That is, the proper placement determination (block 302) can be used to adjust the treatment so that the effective treatment received is the same regardless of variation in treatment unit (FIG. 2, 214) application.

For adjusting the emitter (FIG. 1, 104) sets based on improper position of an emitter (FIG. 1, 104), there are a variety of methods that may be implemented, some of which are described herein to provide an understanding of what can be done with the quality information. In one example, adjusting includes increasing an emitting energy of an improperly positioned emitter (FIG. 1, 104). As a specific example, the sensing system (FIG. 1, 108) and controller (FIG. 1, 110) may indicate that a user has put, as an example, one emitter (FIG. 1, 104) further from the scalp than it should be. In response to the improper placement of this single emitter (FIG. 1, 104), the control system (FIG. 1, 106) may raise the output power of that emitter (FIG. 1, 104) to compensate for the propagation loss that is incurred for the further distance.

As a specific numeric example, it may be the case that the closest that an emitter (FIG. 1, 104) can get to the scalp is 5 millimeters (mm) away, which is the thickness of a spacer used on the inside of the head cap. In one instance, a measured distance from the emitter (FIG. 1, 104) in question to the scalp is 10 mm. Accordingly, the output power to this emitter (FIG. 1, 104) may be increased by the control system (FIG. 1, 106) by 6 decibels (dB) as per the formula: 20 log (10 mm/5 mm). In this example, the 6 dB increase in output power offsets the additional loss that is incurred by the emitter (FIG. 1, 104) being twice as far from the scalp as compared to a desired application. Such an adjustment results in the same incident power and treatment levels in the brain.

In another example, adjusting includes increasing a treatment session length of the improperly positioned emitter (FIG. 1, 104) to offset a lower quality application. Similar to the previous example, the amount of time increase is proportional to how far from the target value the emitter (FIG. 1, 104) is. Treatment session length time may be increased for all emitters (FIG. 1, 104) in the treatment unit (FIG. 2, 214), or may be increased for just those emitters (FIG. 1, 104) that are determined (block 302) to be improperly placed. In yet another example, adjustment includes executing subsequent treatment sessions. For example, in the event that multiple emitters (FIG. 1, 104) are determined (block 302) to be improperly placed, an additional treatment session may be recommended.

Figure 4A:
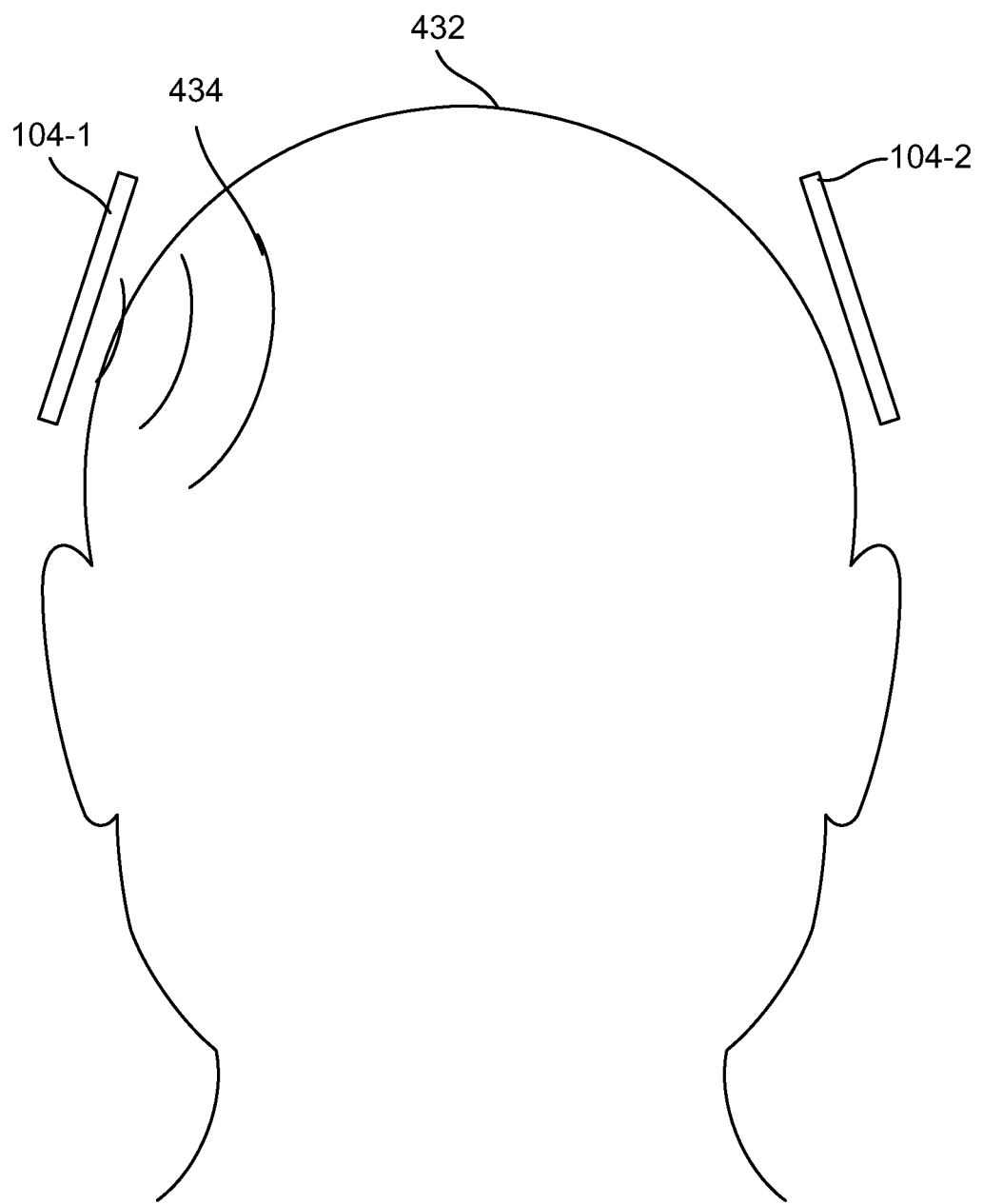
FIGS. 4A and 4B are diagrams of an emitter system disposed on a subject, according to an example of the principles described herein.
Figure 4B:
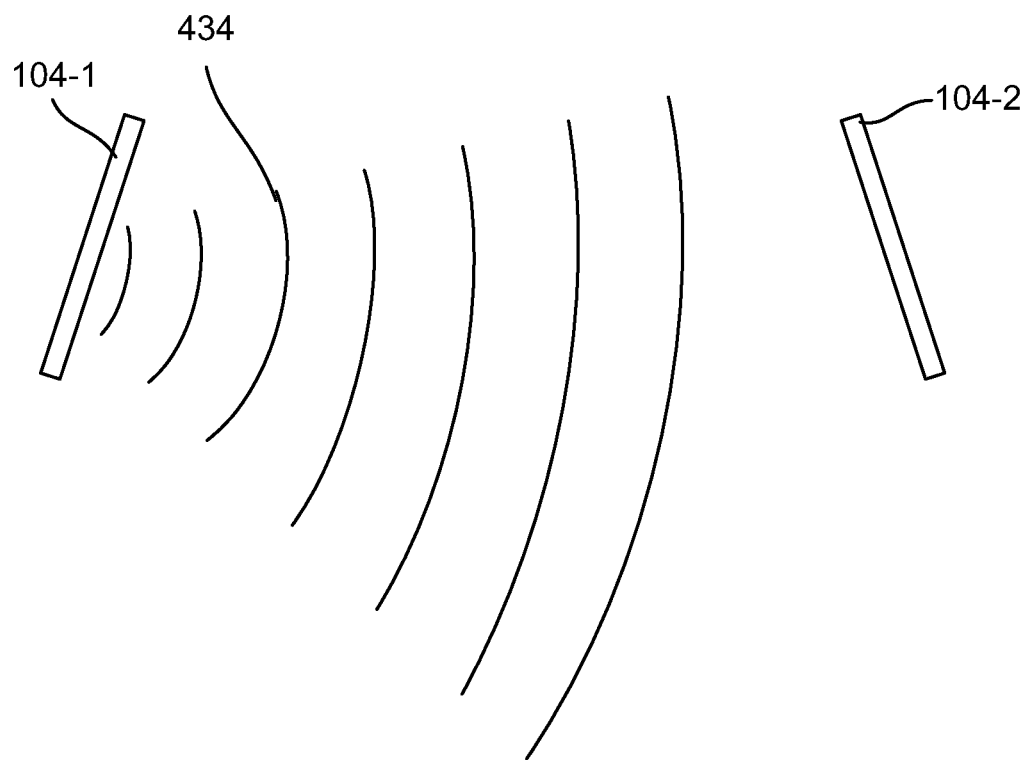

FIGS. 4A and 4B are diagrams of an emitter system (FIG. 1, 100) disposed on a subject (432), according to an example of the principles described herein. Specifically, FIG. 4A depicts a subject (432) head while wearing a head treatment unit (FIG. 2, 214), resulting in a desired treatment, and FIG. 4B depicts how the waves (434) would propagate if the head cap was not applied to the subject (432). For simplicity, in FIGS. 4A and 4B, just two emitters (104-1, 104-2) are depicted as being mounted on opposite sides of the subject (432), however, other emitters (104) may be present during use. As depicted in FIG. 4A, a first emitter (104-1) may be active, that is it may be transmitting a treatment signal, represented by waves (403). As the treatment signals are absorbed by the brain, the remaining power that continues to propagate is reduced as waves (434) travel through the brain. Accordingly, by the time the treatment signals get to the emitter (104-2) on the opposite side of the subject (432), the signal has significantly been reduced by the power that was absorbed by the brain.

Similar to FIG. 4A, in FIG. 4B the first emitter (104-1) is actively transmitting, as shown by the waves (434). However, in FIG. 4B, there is no subject (FIG. 4A, 432) to absorb the waves (434), so the power level is still strong when the signal reaches the emitter (104-2) on the other side of the head cap. Accordingly, power received by the second emitter (104-2) generates a large signal which is passed to the controller (FIG. 1, 110). This large reading is an indication to the controller (FIG. 1, 110) that the head cap is not properly positioned. While a specific example is provided with a head cap properly worn (FIG. 4A) and not worn at all (FIG. 4B), a similar determination could be used to identify a head cap that is worn, but improperly positioned. As described above, this difference can be detected and used to terminate a treatment, adjust a treatment, or provide a notification of improper placement of emitters (FIG. 1, 104).

Figure 5:
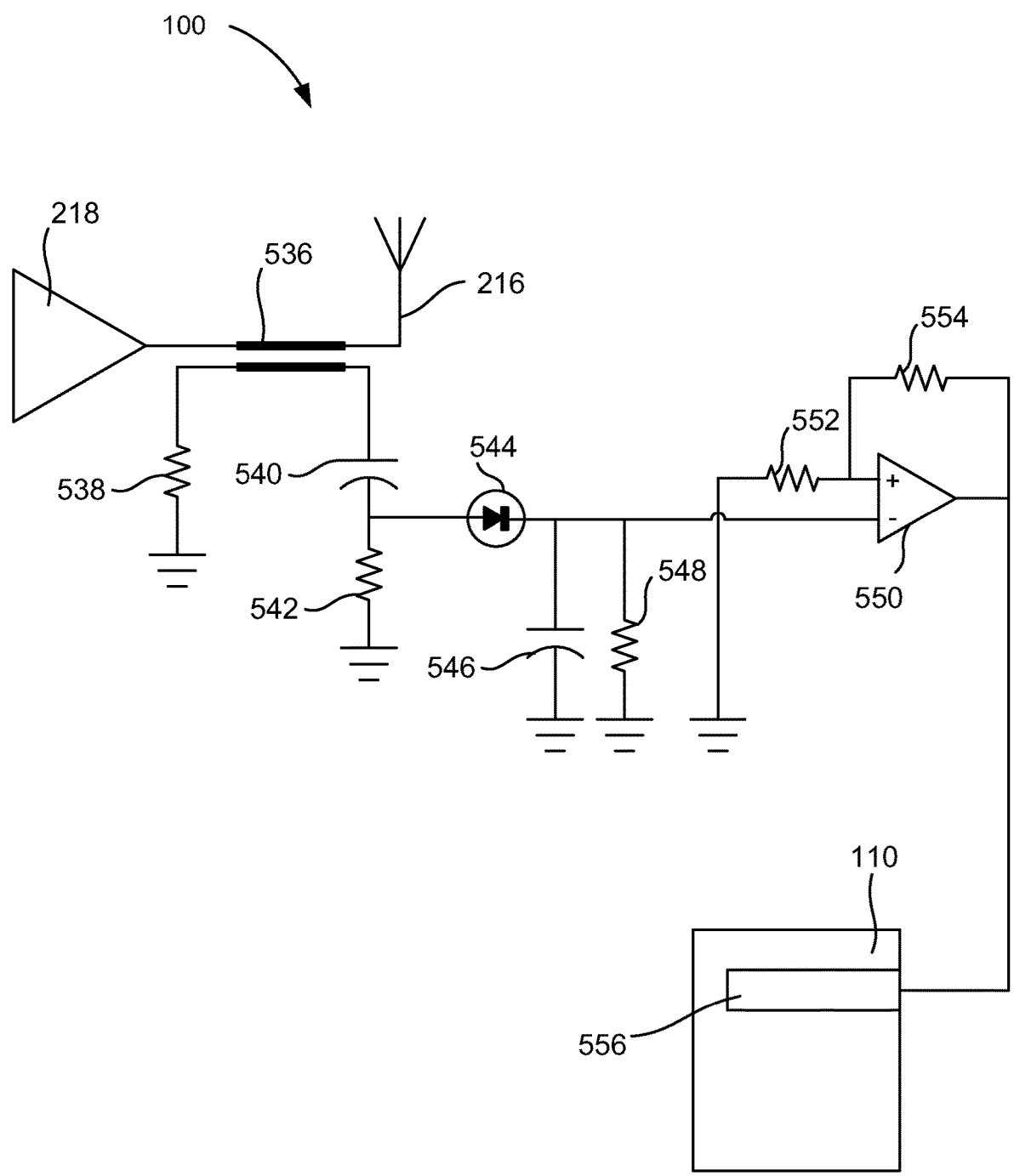
FIG. 5 is a diagram of an emitter system, according to an example of the principles described herein.

FIG. 5 is a diagram of an emitter system (100), according to an example of the principles described herein. As described above, in some examples, the sensing system (FIG. 1, 108) includes a directional power detection system to measure at least one of 1) power reflected from an active emitter (FIG. 1, 104) onto the active emitter (FIG. 1, 104) or 2) power received from an active emitter (FIG. 1, 104) onto an inactive emitter (FIG. 1, 104). FIG. 5 depicts such a directional power detection system in conjunction with a controller (110) and transmitter (218). In the example depicted in FIG. 5, the emitters (FIG. 1, 104) are depicted as antennas (216). However, as described above, the emitters (FIG. 1, 104) may be of varying types including magnetic coils or contact patches.

In this example, the directional power detection system includes a directional coupler (536) which detects power that is flowing in a particular direction. The directional coupler (536) is used to detect the power that is coming back from one or more emitters (FIG. 1, 104).

This detected power may be utilized in two ways. First, when considering the reflected power that is coming back from an antenna (216) that is actively transmitting, the reflected power level is an indication of how well an antenna (216) is working. For example, for an antenna (216) that is working as expected and radiating into the air all of the power that is driven into it, the measured reflected power will be very low. However, in some examples loading or materials that are in proximity to the antenna (216) affect the antenna's (216) ability to radiate power into the air. Accordingly, some of the power will not radiate from the antenna (216) and will be reflected back to the transmitter (218). This reflected power is measured by the directional coupler (536) circuit. Accordingly, a large reflected power measure, relative to an original output amount, may indicate that the head treatment unit (FIG. 2, 214) is not applied properly. This is because in a proper application, all of the antenna (216) power would radiate into the air and into the patient's brain, resulting in a very small amount of power being reflected back. Accordingly, if reflected power is high, this may be an indication that the head treatment unit (FIG. 2, 214) is not applied properly.

In another example, reflected or received power as measured by a directional coupler (536) circuit may be done by antennas (216) that are not transmitting. In this case, power received by antennas (216) that are not transmitting indicates the power that the non-transmitting antennas (216) receive from the transmitting antenna (216). If the head treatment unit (FIG. 2, 214) is properly applied to the patient, the power from the transmitting antenna (216) will be absorbed by the patient's brain and will not be received at a high level by the other antennas (216). Alternatively, if the head treatment unit (FIG. 2, 214) is simply sitting on a table and not on the patient's head, or improperly placed on a patient's head, the power from the transmitting antenna (216) will not be absorbed and will transmit across the empty head treatment unit (FIG. 2, 214) to the other side, and will be received by the other antennas (216) at a high power level. Accordingly, if power received by the non-transmitting antennas (216) is high, this may be an indication that the head treatment unit (FIG. 2, 214) is not applied properly.

During use, the transmitter (218) generates and amplifies a waveform, which may be of different frequencies in including electromagnetic and magnetic. The waveform passes through directional coupler (536) before driving the antenna (216). Any power that is reflected by the antenna (216) and not radiated will reflect back and pass through the directional coupler (536). While specific reference is made to a directional coupler (536), an isolator may also be used.

The directional coupler (536), in the configuration shown in FIG. 5, just couples the power that flows back from the antenna (216). A first resistor (538) provides the proper load for the coupler (536) and is part of the configuration for setting up the directional coupler (536) to just measure reflected power. The coupled power flows through the DC blocking capacitor (540). A second resistor (542) provides a ground bias to the input of rectifying diode (544), ensuring that the diode just conducts on the peaks of the RF signal. The RF signal is rectified by the rectifying diode (544), and the rectified energy is used to charge the second capacitor (546). A third resistor (548) provides a discharge path for the second capacitor (546) so the rectified voltage just stays on the second capacitor (546) for a short amount of time. Just long enough for the controller (110) to read the rectified voltage while it maintains a stable value.

The rectified voltage is then amplified by an amplifier (550), and the gain of the amplifier is set by a fourth and fifth resistor (552, 554). The amplified signal ensures that signals are strong compared to any noise floor in the system. The analog-to-digital converter (ADC) (556) converts the analog voltage to a digital value that can be used by the controller (110). The digital value is a scaled representation of the reflected power received at the directional coupler (536) such that subsequent control of the emitter array (FIG. 1, 102) can be made.

Figure 6:
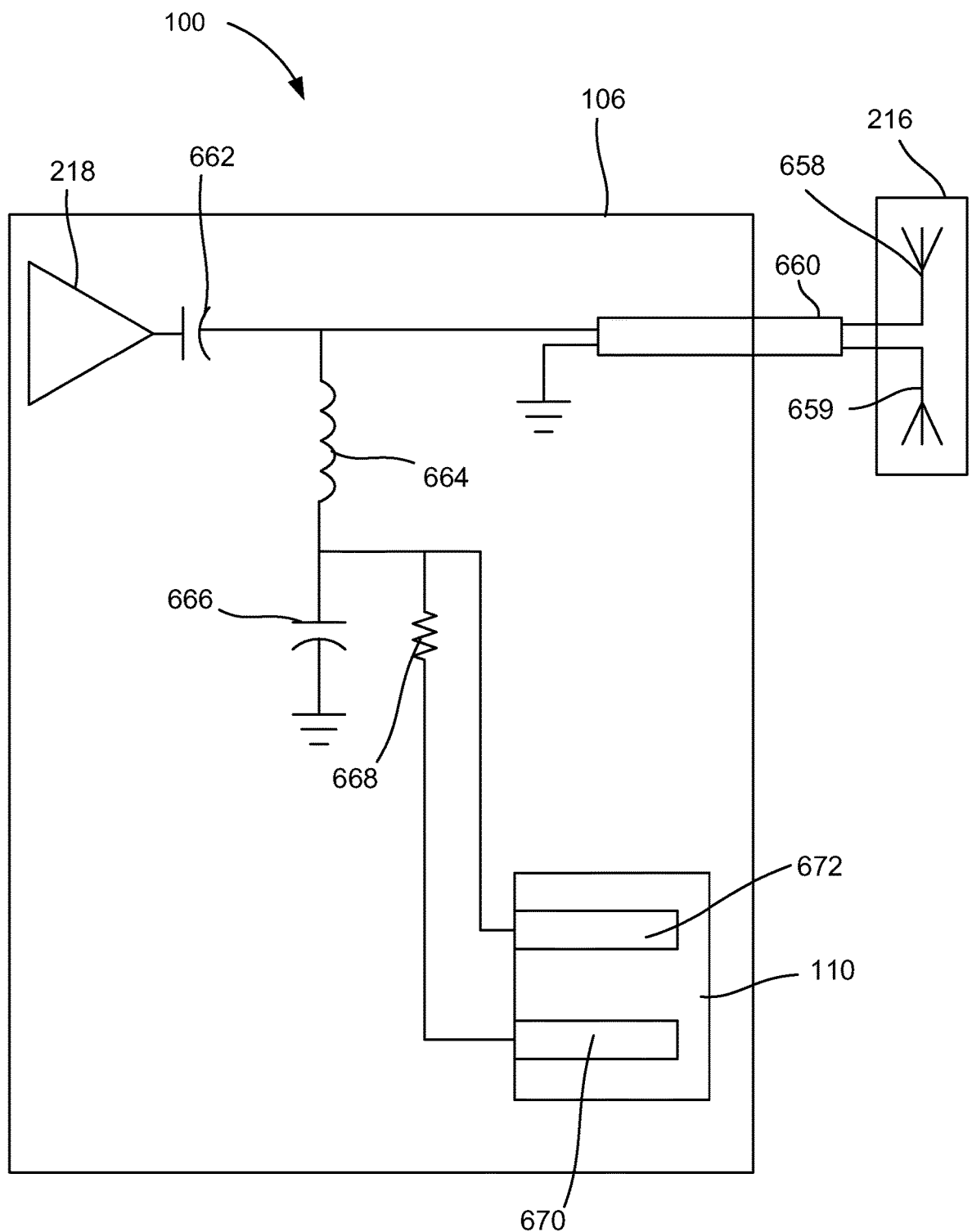
FIG. 6 is a diagram of an emitter system, according to another example of the principles described herein.

FIG. 6 is a diagram of an emitter system (100), according to another example of the principles described herein. As described above, in some examples, the sensing system (FIG. 1, 108) includes a capacitive load sensing system to determine a capacitive loading on each emitter (FIG. 1, 104). As with the example depicted in FIG. 5, in FIG. 6, antennas (216) are depicted as the emitters (FIG. 1, 104), however, other types of emitters (FIG. 1, 104) may also be used.

In this example, the antennas (216) implement capacitive sensing to determine if they are all equally close to the scalp. Such a capacitive sensing system involves two conductive surfaces and a changing voltage to detect the amount of capacitance between the surfaces. When substantially close to the scalp of the patient, the surfaces on the antenna (216) would see higher capacitive loading than if further from the scalp. Accordingly, if all of the antennas (216) in the treatment unit (FIG. 2, 214) have capacitive loading similar to that of being near the scalp, there is a good indication that the treatment unit (FIG. 2, 214) is applied properly.

In another example, the capacitive loading on the antenna (216) is determined by examining the phase of a radio frequency signal. More specifically, the phase of the current is examined as it compared to the phase of the voltage of the radio frequency signal. As the loading characteristics of the antenna (216) change, the phases change, which subsequently can be detected by the detection circuitry.

Using the existing antenna (216) traces, capacitive sensing could be embodied by changing the DC bias on the active element (658) of the antenna (216) with respect to the counterpoise (659) through a large resistor and sensing how long it takes for the DC bias after the resistor to settle, which would be a function of the loading capacitance. While capacitive sensing typically uses DC changes, or frequencies much lower than typical RF frequencies used in treatments, a scheme of using the treatment frequencies could be used for the capacitive sensing. In a different example, the capacitive sensing is done not with conductive surfaces on the antenna (216) but instead locating the surfaces in other areas on the treatment head cap (FIG. 2, 214).

FIG. 6 shows a circuit that uses the metal surfaces on the antenna (216) as the surfaces used for capacitive sensing. While FIG. 6 depicts a single transmitter (218) driving a single antenna (216), the implementation may be duplicated and scaled to as many antennas (216), or other emitters (FIG. 1, 104) as needed.

In this figure, the control system (106) is coupled to the antenna (216) via a coaxial cable (660). Within the control system (106), a single transmitter (218) generates and amplifies the RF waveform. At the output of the transmitter (218) is a DC-blocking capacitor (662), which allows the transmitter (218) and the antenna (216) to be sitting at different DC bias levels. Connecting to the feed line to the antenna (216) is an RF blocking inductor (664) which allows the DC bias to be applied but blocks the RF from the DC-biasing circuitry. Bypass capacitor (666) filters out any RF that remains after RF blocking inductor (664). DC bias resistor (668) brings the DC bias signal from the controller (110). The controller (110) generates the DC bias signal using the digital output (670). This digital output is in the form of a digital pin that is driven either to ground or the supply rail of the controller (110).

When measuring capacitance at the antenna (216), the controller (110) measures the capacitance that is present between the radiating element (658) of the antenna (216) and the counterpoise (659). The controller (110) measures this by transitioning the digital output, for example, from ground to the positive supply rail. For simplicity sake, the positive supply rail can be abbreviated as Vs. This digital voltage changes very fast, and this voltage is applied to the antenna (216) through the DC bias resistor (668). The rise time of the DC bias on the antenna is a function of the resistance of the DC bias resistor and the capacitance across the antenna (216), since none of the other components in the circuit have an influence on the rise time. The voltage on the antenna will rise as per the formula: $Vs*(1-1/(e^{(t/(R*C))}))$. In this formula Vs is the digital output from the controller, e is Euler's Number (2.71828), t is time since digital output was driven to Vs, R is the value of the DC bias resistor (668) and C is the capacitive load on the antenna.

In this example, the controller (110) starts the capacitance measurement by setting time t to 0 and driving the digital output to Vs. Then the controller (110) samples the DC bias voltage on the antenna (216) using the analog-to-digital converter (ADC) (672) at periodic intervals in time. With the controller (110) knowing the values of Vs, R, and the DC bias voltage at several points in time, it can use the above formula to repeatedly calculate the measured capacitive load on the antenna (216). Because the capacitance load on the antenna (216) may be very small, the average of many readings and calculations will result in a more accurate reading. To further improve accuracy of the measurement, the process can be repeated in the other direction by driving the digital output from Vs to ground and measuring the DC bias decay and calculating and averaging capacitance values. To further increase accuracy, the controller (110) can output a very low frequency square wave on the digital output and continuously read the DC bias through the ADC (672) to continuously calculate measured capacitance.

While FIG. 6 depicts determining capacitance reading of loading capacitance on the antenna (216), these techniques can be used to measure capacitance on any conductive surfaces placed inside the head treatment unit (FIG. 2, 214) for detection. That is, the capacitive sensing surface may measure capacitive loading on a respective antenna (216) itself or on a region of the substrate on which the array of emitters (FIG. 1, 104) is disposed.

Figure 7:
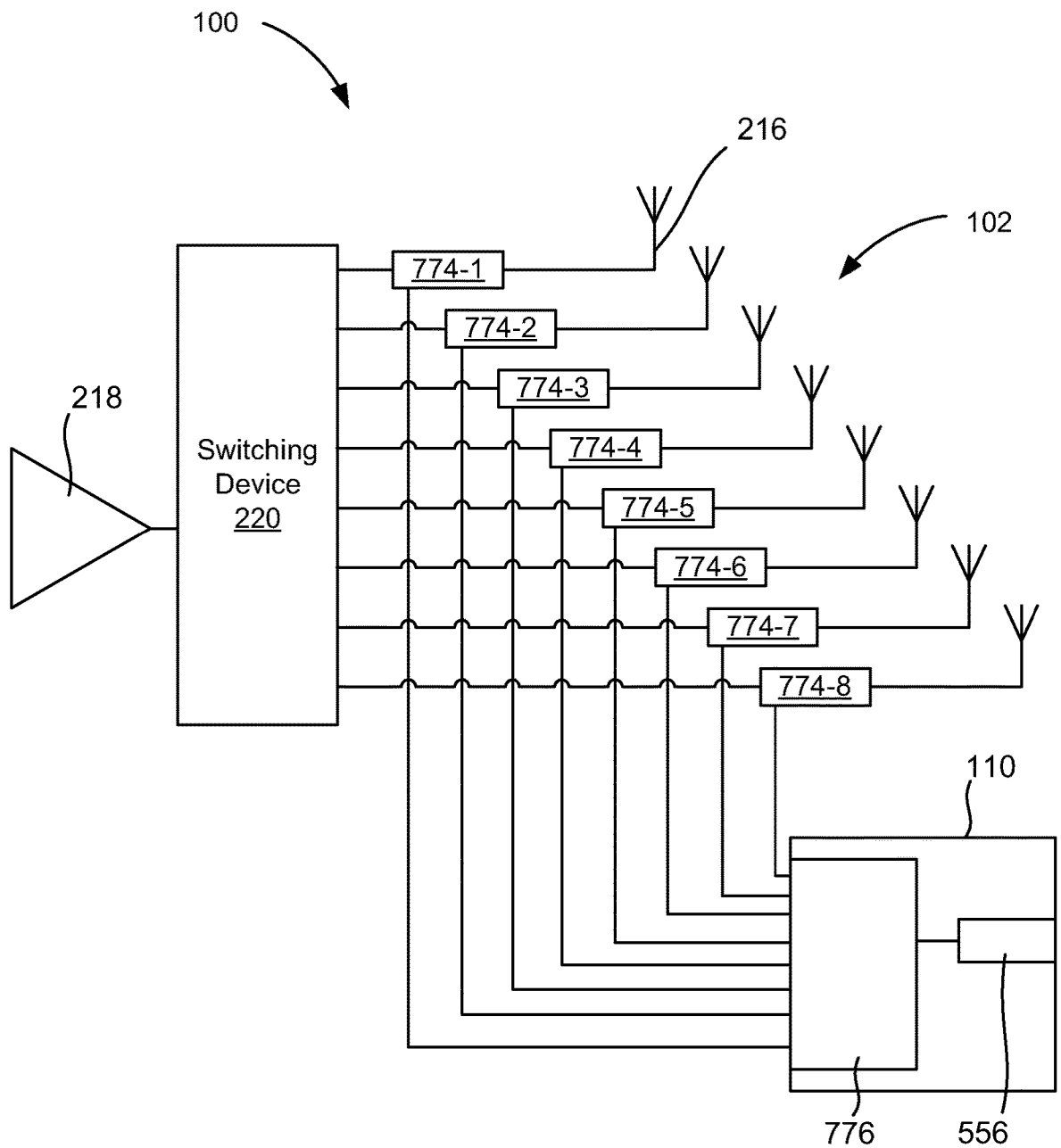
FIG. 7 is a diagram of an emitter system, according to another example of the principles described herein.

FIG. 7 is a diagram of an emitter system (100), according to another example of the principles described herein. In some examples, the single transmitter (218) may drive multiple emitters (FIG. 1, 104) such as the antennas (216) in the array (102) depicted in FIG. 7. For simplicity, a single antenna (216) in the array (102) is indicated with a reference number. Accordingly, the sensing system (FIG. 1, 108) may also detect the positioning of the multiple antennas (216). While FIG. 7 depicts a directional power sensing system (FIG. 108), the other sensing systems (FIG. 1, 108) may also be multiplexed from multiple antennas (216) into the controller (110) as depicted in FIG. 7.

In this figure, the transmitter (218) output is first fed into a switching device (220), where the signal, which may be an RF signal, is switched onto one of the multiple outputs of the switching device (220). In one example, the switching device (220) has a single output active. However, in other examples, the switching device (220) may activate more than one of its internal switches to put the input RF signal onto several of its outputs.

Each output of the switching device (220) feeds into a directional-power detect circuit (774-1, 774-2, 774-3, 774-4, 774-5, 774-6, 774-7, 774-8) before being fed into the array (102). Each of the directional power detect circuits (774) may include various components depicted in FIG. 5. The output of each of the directional power detect circuits (774) is fed into the controller (110), where an analog multiplexer (MUX) (776) selects which signal to bring into the ADC (556). With this arrangement, the controller (110) can read each of the directional power detect circuits (774) individually, in a sequential manner.

In another example, instead of having a full directional power detect circuit (774) for each antenna (216), elements of the circuit may be made common and used for all of the circuits. For example, the amplifier (FIG. 5, 550) could be instantiated once, and all of the rectified voltages could be fed to this amplifier (FIG. 5, 550) through a selector. This would require the addition of a selector, but would reduce the number of amplifiers needed in the system to one. In other words, the sensing system (FIG. 1, 108) may include a sensing device per emitter (FIG. 1, 104) or may have at least a portion of the sensing system (FIG. 1, 108) shared among different emitters (FIG. 1, 104).

When the controller (110) reads the outputs of the directional power detect circuits (774), it is reading either the reflected power, if reading from an antenna path that is active, or it is reading received power, if reading from an antenna path that is not active. If reading received power from an inactive antenna (216), the controller (110) is reading the power that is radiated by an active antenna and subsequently received by an inactive antenna. In this example, the controller (110) may just measure relatively strong received signals.

Figure 8A:
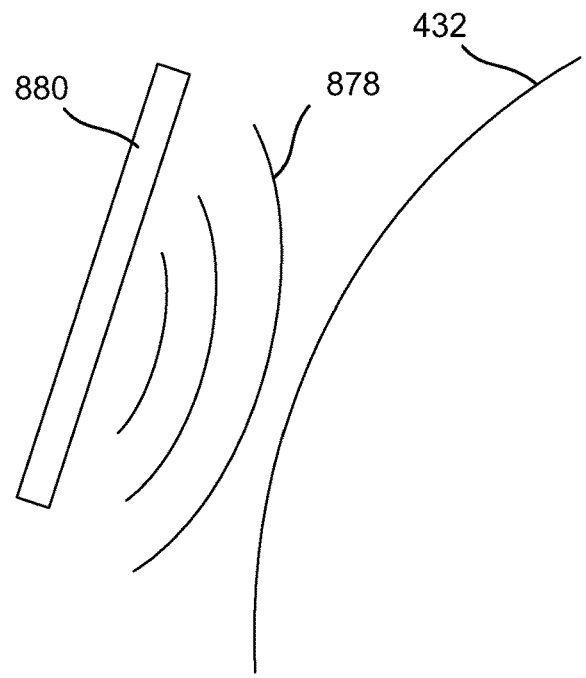
FIGS. 8A and 8B are diagrams of a sensing system, according to another example of the principles described herein.
Figure 8B:
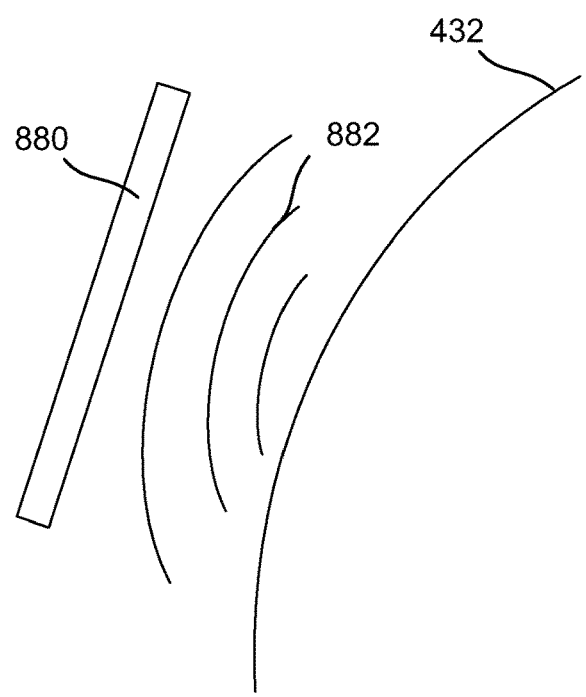

FIGS. 8A and 8B are diagrams of a sensing system (FIG. 1, 108), according to another example of the principles described herein. In this example, optical sensing could also be used to detect head treatment unit (FIG. 2, 214) application. For example, infrared transceivers could be placed in various locations in the treatment unit (FIG. 2, 214). These transceivers could be used to transmit an infrared pulse and to detect the reflection off of the hair and scalp when properly applied. In another example, a transceiver could attempt to send infrared to the other side of the cap, assuming it would not make it across if the head cap is properly applied. While specific reference is made to infrared waveforms, light within the visible light spectrum could be used in a similar way, as could ultrasonic frequencies. FIGS. 8A and 8B depict an example of such a scenario.

In this example, a transmit wave (878) may be a short burst of energy from the transceiver (880) that propagates towards the subject (432) as depicted in FIG. 8A. FIG. 8B depicts the wave (882) as an energy burst being reflected back from the subject (432) and falls incident on the transceiver (880). The transceiver (880) uses the time between sending and receiving the burst to calculate the distance to the subject (432). The transceiver (880) of the sensing system (FIG. 1, 108) may be coupled to the control system (FIG. 1, 106) such that this distance information can be used to determine proper placement of the head treatment unit (FIG. 2, 214).

Figure 9:
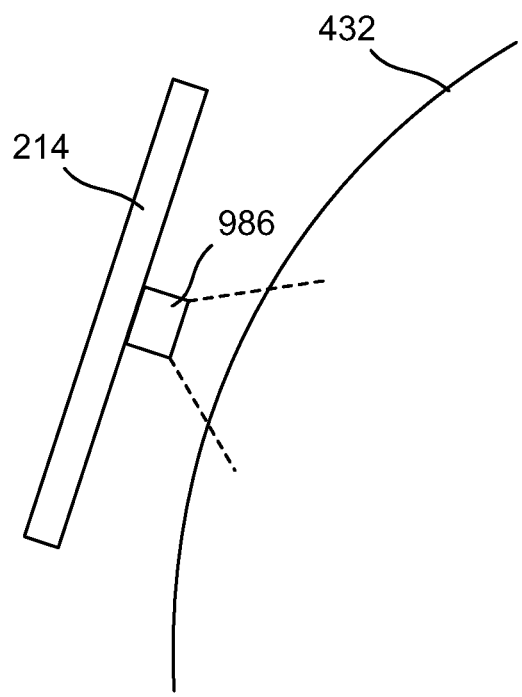
FIG. 9 is a diagram of a sensing system, according to another example of the principles described herein.

FIG. 9 is a diagram of a sensing system (FIG. 1, 108), according to another example of the principles described herein. In another example, the sensing system (FIG. 1, 108) may include photodetectors (986) that detect the presence of light. These photodetectors (986) may be placed on the inside of the treatment unit (214). When properly applied, these photodetectors (986) would receive very little ambient light due to the blockage of light by the subject (432). FIG. 9 depicts such an example.

In this example, the photodetector (986) has a side that is open for light input, and the cone of visibility to the opening for light input is shown in FIG. 9 by dashed lines. Any light that is within the cone is measured by the photodetector (986), but light outside the cone is not detected. As the photodetector (986) that is mounted on the treatment unit (214) gets closer to the subject (432), the amount of ambient light that will be in the cone of visibility will decrease. The photodetector (986) of the sensing system (FIG. 1, 108) may be coupled to the control system (FIG. 1, 106) such that this distance information can be used to determine proper placement of the head treatment unit (FIG. 2, 214).

Figure 10:
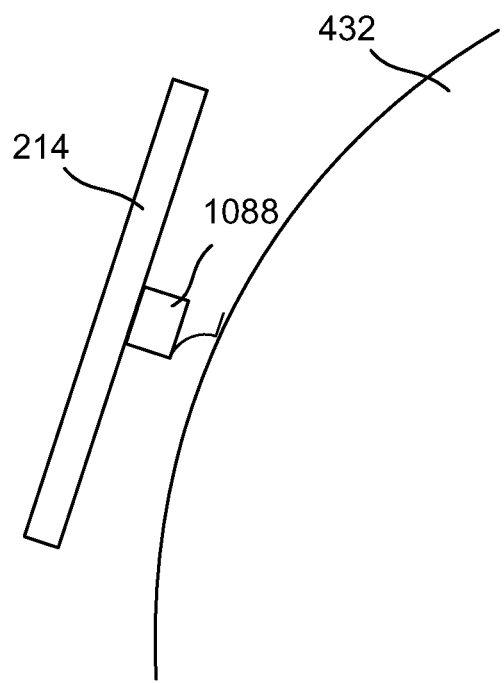
FIG. 10 is a diagram of a sensing system, according to another example of the principles described herein.

FIG. 10 is a diagram of a sensing system (FIG. 1, 108), according to another example of the principles described herein. In another example, the sensing system (FIG. 1, 108) may include a mechanical sensing system. Such a system may include switches (1088) placed in various locations within the treatment unit (214). When properly applied to the subject (432), all of the contact switches (1088) would be activated, indicating proper application. FIG. 10 depicts such an example.

As depicted in FIG. 10, the head treatment unit (214) may provide a mounting point for the switch (1088). As the head treatment unit (214) and the switch (1088) are brought closer to the subject (432), the actuator of the switch (1088) will activate, providing contact within the switch (1088). The contacts of the switch (1088) of the sensing system (FIG. 1, 108) may be coupled to the control system (FIG. 1, 106) such that this distance information can be used to determine proper placement of the head treatment unit (214).

Figure 11:
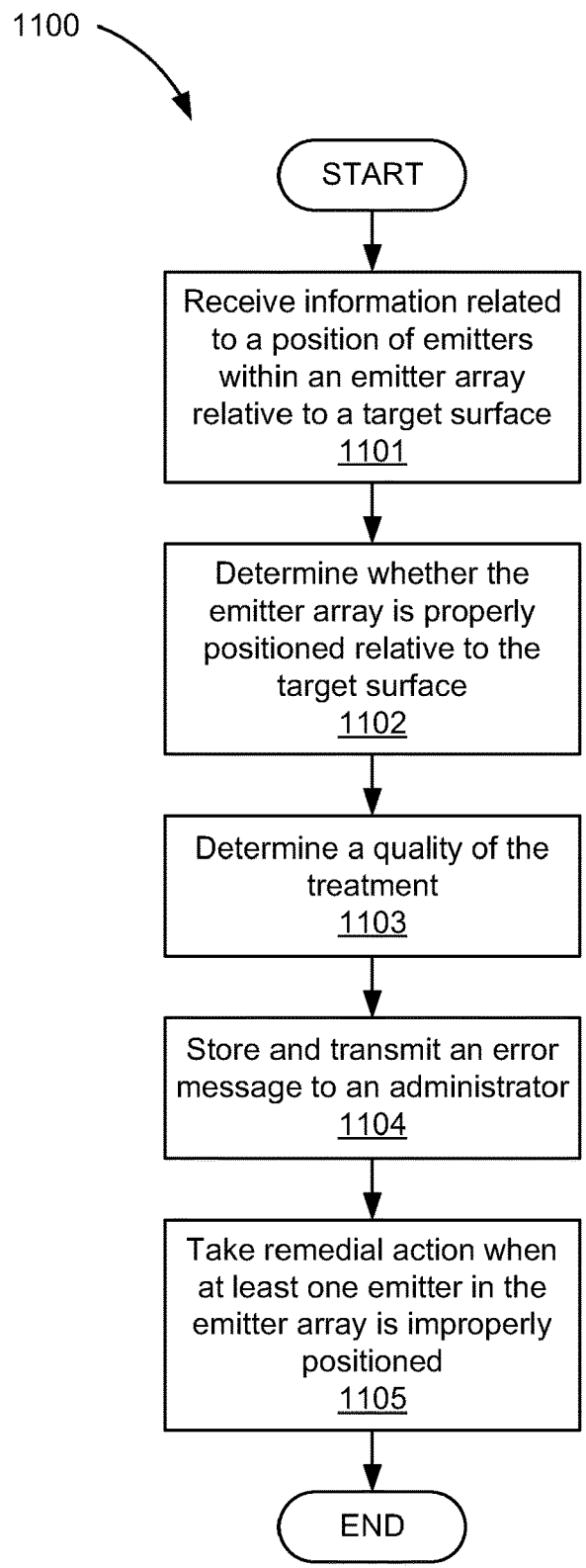
FIG. 11 is a flowchart of a method of controlling the emitter system, according to another example of the principles described herein.

FIG. 11 is a flowchart of a method (1100) of controlling the emitter system (FIG. 1, 100), according to another example of the principles described herein. According to the method (1100) information is received (block 1101) indicating emitter (FIG. 1, 104) position relative to a target surface. From this information it is determined (block 1102) whether the emitter (FIG. 1, 104) is properly positioned relative to the target surface.

In some examples, in addition to determining (block 1102) improper placement, a degree of improper placement may be determined. That is, it may be the case that a certain degree of improper placement of an emitter (FIG. 1, 104) or a certain quantity of emitters (FIG. 1, 104) being improperly placed to a certain degree is acceptable such that an adequate treatment may still be applied. Accordingly, this degree of improper placement may be quantified. For example, based on the number of emitters (FIG. 1, 104) improperly placed and the degree to which they are improperly placed, a quality of the treatment may be determined (block 1103). The quality of treatment may alter the remedial action that is taken. That is, if the quality of treatment is still relatively high, fewer adjustments may be made to the emitters (FIG. 1, 104). By comparison, if the quality of treatment is relatively low, more drastic alterations may be implemented.

When such an error in placement is detected, an error message may be stored (block 1104) and logged to an administrator. For example, the improper head treatment unit (FIG. 2, 214) application may be logged in the control system (FIG. 1, 106), and the error may be communicated to the physician overseeing the treatment via connectivity that the control system (FIG. 1, 106) may have. The transmission of this information may provide even more information to an overseeing physician who can tailor a treatment plan accordingly.

Then, as described above in connection with FIG. 3, remedial actions, in whatever form, may be taken (block 1105) based on the detection of an improperly placed emitter (FIG. 1, 104).

Figure 12:
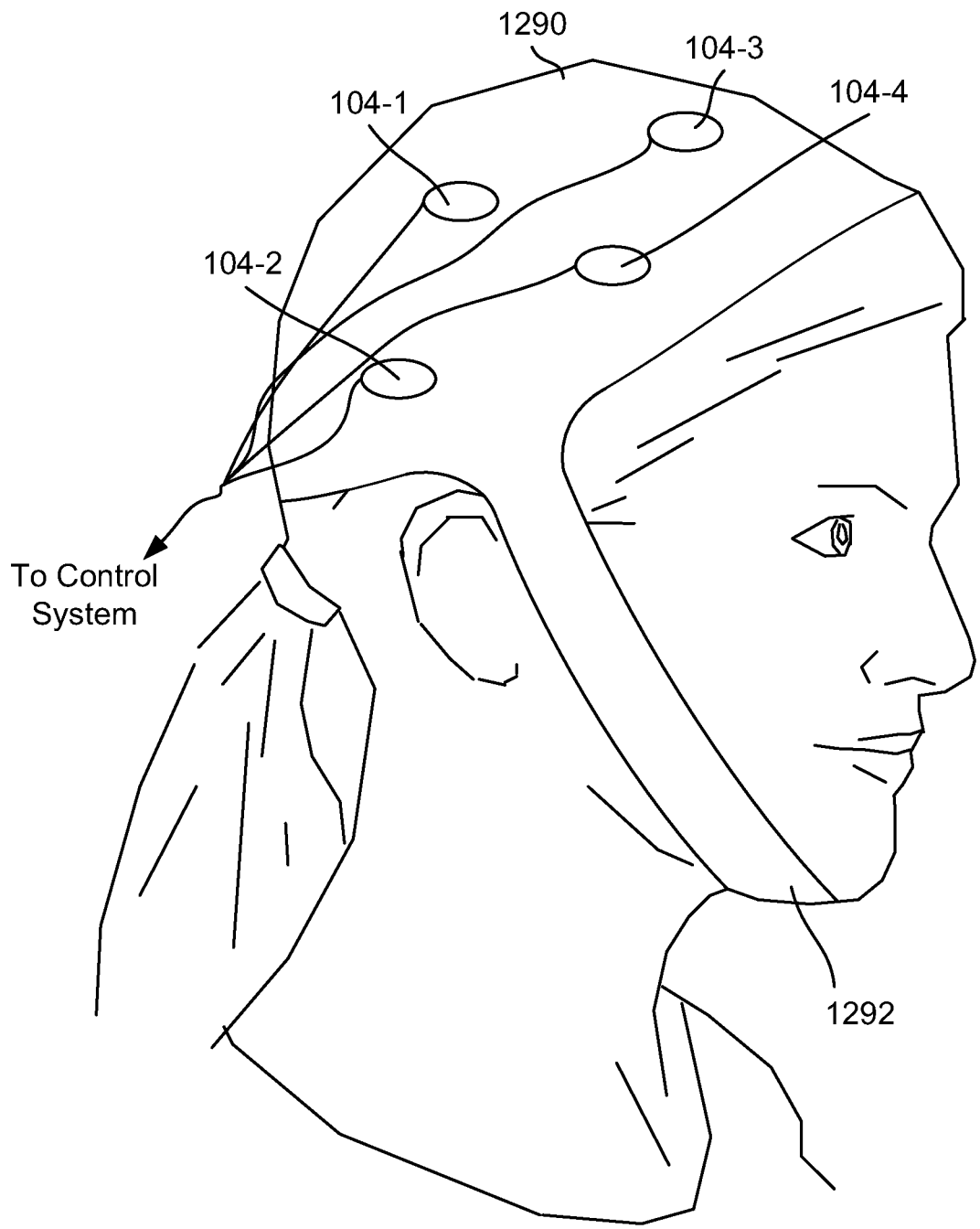
FIG. 12 depicts an electromagnetic treatment system with the emitter system, according to an example of the principles described herein.

FIG. 12 depicts an electromagnetic treatment system (FIG. 2, 212) with the emitter system (FIG. 1, 100), according to an example of the principles described herein. As described above, the electromagnetic treatment system (FIG. 2, 212) includes a treatment unit (FIG. 2, 214). In the example depicted in FIG. 12, the treatment unit (FIG. 2, 214) is a head cap (1290) to be worn by the subject. In this example, the treatment surface is the scalp of the subject. The head cap (1290) also includes an array (FIG. 1, 102) of emitters (104). As described above, each emitter (104) is to emit electromagnetic waves. Note that FIG. 12 depicts emitters (104) on one side of the head region. The opposite side of the head region may include similarly positioned emitters (104).

In some examples, the head cap (1290) has a chin strap (1292) that sits under the subject's chin and is secured to hold the head cap (1290) on. In some examples, a detection system is disposed on the chin strap (1292) of the head cap (1290) to indicate when the head cap (1290) is properly attached to the subject.

That is, the detection system may be built into this chin strap (1292) to indicate to the control system (FIG. 1, 106) when the chin strap (1292) is connected, and therefore when the head cap (1290) has been properly applied. This detection system may be in the form of an electrical contact in a snap, in a proximity detection scheme with two conductive surfaces, or any similar mechanism to detect proper securing of the chin strap (1292). In some examples, a combination of the chin strap (1292) detection combined with other methods may produce more reliable results. The electromagnetic treatment system (FIG. 2, 212) also includes the control system (FIG. 1, 106) as depicted in FIG. 1.

The preceding description has been presented only to illustrate and describe the subject matter presented herein. It is not intended to be exhaustive or to limit the subject matter to any precise form disclosed. Many modifications and variations are possible in light of the above teaching.

The examples descried herein were chosen and described in order to best explain the principles of the subject matter and its practical application. The preceding description is intended to enable others skilled in the art to best utilize the subject matter in various embodiments and with various modifications as are suited to the particular use contemplated.

What is claimed is:

1. An emitter system, comprising:
   an array of emitters, each emitter to emit waves towards a target surface; and
   a control system, comprising:
   a sensing system to determine whether emitters in the array are properly positioned relative to the target surface, the sensing system comprising a directional power detection system to:
   measure power reflected from an active emitter onto the active emitter; and
   measure power received from an active emitter onto an inactive emitter,
   wherein the sensing system is to determine whether the emitters in the array are properly positioned relative to the target surface by comparing the measurements indicating power received for each emitter against a reference value; and
   a controller to adjust emitter sets of the array of emitters based on an output of the sensing system.

2. The emitter system of claim 1, wherein the sensing system comprises a sensing device per emitter.

3. The emitter system of claim 1, wherein at least a portion of the sensing system is shared with different emitters.

4. The emitter system of claim 1, wherein:
   the sensing system comprises a capacitive sensing system to determine a capacitive loading on each emitter; and
   the capacitive sensing system includes conductive surfaces disposed on at least one of:
   a respective antenna; and
   a region of a substrate on which the array of emitters is disposed.

5. The emitter system of claim 1, wherein:
   the sensing system comprises:
   a photodetector;
   a mechanical switch; and
   at least one transceiver to transmit at least one of:
   infrared waveforms;
   visible spectrum waveforms; and
   ultrasonic waveforms.

6. The emitter system of claim 1, wherein the control system further comprises:
   a wireless transmitter;
   a switching device to direct a control signal to a selected emitter set;
   a charging device;
   an internal battery; and
   a control panel.

7. A method, comprising:
   receiving, from a sensing system of an emitter array, information related to a position of emitters within the emitter array relative to a target surface by receiving measurements indicating power received from an active emitter onto an active emitter and an inactive emitter;

determining from the received information whether the emitter array is properly positioned relative to the target surface by comparing the measurements indicating power received for each emitter against a reference value; and taking remedial action when the received information indicates at least one emitter in the emitter array is improperly positioned relative to the target surface.

8. The method of claim 7, wherein:

the method further comprises passing a signal to a capacitive sensing system coupled to the emitters in the array;

receiving information related to a position of emitters within the emitter array relative to a target surface comprises receiving a capacitive loading measurement for each emitter from a capacitive sensing system; and determining whether the emitter array is properly positioned relative to the target surface comprises comparing the capacitive loading measurement for each emitter against a reference value.

9. The method of claim 8, wherein the signal is at least one of:

a signal having a frequency less than a frequency of a control signal from the transmitter to drive the emitter array; and the control signal from the transmitter to drive the emitter array.

10. The method of claim 7, wherein the remedial action comprises at least one of:

preventing activation of an improperly positioned emitter;

providing a notification of an improperly positioned emitter; and adjusting for an improperly positioned emitter.

11. The method of claim 10, wherein adjusting for an improperly positioned emitter comprises at least one of:

increasing an emitting energy of the improperly positioned emitter;

increasing a treatment session length of the improperly positioned emitter; and executing subsequent treatment sessions including the improperly positioned emitter.

12. The method of claim 7, further comprising, determining, based on a number of emitters improperly positioned relative to the target surface and a degree of improper placement of the emitters within the array, a quality of the treatment by the emitters.

13. The method of claim 7, further comprising storing and transmitting an error message to an administrator of the emitter array.

14. An electromagnetic treatment system comprising:

a treatment unit to be worn by a subject, the treatment unit comprising:

a material to be placed proximate a treatment surface; and an array of antennas, each antenna to emit electromagnetic waves towards the treatment surface; and a control system, comprising:

a single transmitter to drive the antennas;

a switching device to direct a control signal to a selected antenna set;

a sensing system to determine whether antennas in the array are properly positioned relative to the treatment surface, the sensing system comprising a directional power detection system to:

measure power reflected from an active emitter onto the active emitter; and measure power received from an active emitter onto an inactive emitter, wherein the sensing system is to determine whether the emitters in the array are properly positioned relative to the target surface by comparing the measurements indicating power received for each emitter against a reference value; and a controller to adjust antenna sets of the array of antennas based on an output of the sensing system.

15. The electromagnetic treatment system of claim 14, wherein:

the treatment unit is a head cap to be worn by the subject; and the treatment surface is a scalp of the subject.

16. The electromagnetic treatment system of claim 15, further comprising a detection system in a chin strap of the head cap to indicate when the head cap is properly attached to the subject.

17. The electromagnetic treatment system of claim 14, wherein the electromagnetic treatment system is for treatment or prevention of neurodegenerative diseases and conditions and for the enhancement of impaired cognitive function.

18. An electromagnetic treatment system, comprising:

a treatment unit to be worn by a subject, the treatment unit comprising:

a material to be placed proximate a treatment surface;

an array of at least one emitter, each emitter to emit waves towards the treatment surface, wherein the treatment disaggregates toxic protein aggregates; and a sensing system to determine whether the emitters in the array are properly positioned relative to the target surface by comparing measurements indicating power received for each emitter against a reference value.

19. The electromagnetic treatment system of claim 18, wherein:

the treatment disaggregates toxic protein aggregates by destabilizing their hydrogen bonds; and the toxic protein aggregates are at least a cause of neurodegenerative diseases and impaired cognitive function.

* * * * *